United States Patent
Furukawa et al.

(10) Patent No.: US 7,488,492 B2
(45) Date of Patent: Feb. 10, 2009

(54) COSMETIC RAW MATERIAL COSMETIC PRODUCT AND METHOD FOR MANUFACTURING A COSMETIC PRODUCT

(75) Inventors: Haruhiko Furukawa, Chiba Prefecture (JP); Yoshitsugu Morita, Chiba Prefecture (JP); Takayuki Aso, Chiba Prefecture (JP)

(73) Assignee: Dow Corning Toray Company, Ltd., Tokyo (JP)

( * ) Notice: Subject to any disclaimer, the term of this patent is extended or adjusted under 35 U.S.C. 154(b) by 752 days.

(21) Appl. No.: 10/496,022

(22) PCT Filed: Nov. 27, 2002

(86) PCT No.: PCT/JP02/12400

§ 371 (c)(1),
(2), (4) Date: May 19, 2004

(87) PCT Pub. No.: WO03/045337

PCT Pub. Date: Jun. 5, 2003

(65) Prior Publication Data

US 2005/0008597 A1 Jan. 13, 2005

(30) Foreign Application Priority Data

Nov. 28, 2001 (JP) .............................. 2001-361948
Feb. 28, 2002 (JP) .............................. 2002-054679

(51) Int. Cl.
- *A61K 8/02* (2006.01)
- *A61K 8/19* (2006.01)
- *A61K 8/25* (2006.01)
- *A61Q 19/00* (2006.01)
- *A61Q 1/00* (2006.01)
- *C08G 77/00* (2006.01)
- *C08G 77/04* (2006.01)
- *C08G 77/42* (2006.01)

(52) U.S. Cl. ....................... 424/401; 424/70.12; 528/10; 528/32

(58) Field of Classification Search ................. 424/401, 424/70.12; 528/32, 10
See application file for complete search history.

(56) References Cited

U.S. PATENT DOCUMENTS 6,033,650 A * 3/2000 Calello et al. ................. 424/64
6,291,021 B1 * 9/2001 Morita et al. ............... 427/387

FOREIGN PATENT DOCUMENTS

JP 2001139413 * 5/2001

* cited by examiner

*Primary Examiner*—Sreeni Padmanabhan
*Assistant Examiner*—Sahar Javanmard
(74) *Attorney, Agent, or Firm*—Howard & Howard Attorneys, P.C.

(57) ABSTRACT

A cosmetic raw material using a vinyl polymer containing carbosiloxane dendritic structures and fluorinated organic group as the main or most important ingredient, a cosmetic product obtained by compounding with the cosmetic raw material, and a method for manufacturing a cosmetic product, in which said cosmetic raw material is mixed with other cosmetic raw materials. The cosmetic raw material exhibits superior compounding stability in cosmetic products and capable of imparting excellent feel and surface protective properties to cosmetic products. The cosmetic product exhibits superior adhesion to the hair and skin.

6 Claims, No Drawings

COSMETIC RAW MATERIAL COSMETIC PRODUCT AND METHOD FOR MANUFACTURING A COSMETIC PRODUCT

The present invention relates to a cosmetic raw material, a cosmetic product, and a method for manufacturing a cosmetic product. Specifically, it relates to a cosmetic raw material exhibiting superior compounding stability in cosmetic products and capable of imparting excellent feel on application and surface protective properties to cosmetic products, to a cosmetic product obtained by compounding with the cosmetic raw material, and to a method for manufacturing the cosmetic product. Cosmetic where used herein includes the application to the body for purposes other than beautifying, such as administering of materials to skin.

In the past, vinyl co-polymers of radical polymerizable monomers and organopolysiloxanes containing radical polymerizable groups have been known to be used as cosmetic raw materials. For instance, Japanese Patent Application Publication No. Hei 5-000924 offers a base oil for a hair dressing agent consisting of a vinyl polymer obtained by polymerizing methacrylic acid and tertiary butyl acrylate with a dimethylpolysiloxane oligomer containing methacrylic groups. While this vinyl co-polymer does give water repellent properties and slip to cosmetic products, its compatibility with other cosmetic raw materials is low, and its compounding stability is inferior. In addition, as a result of insufficient adhesion to the hair and skin, it easily washes off and has inferior surface protective properties. A cosmetic raw material using a vinyl polymer with carbosiloxane dendritic structures in side chains as its main ingredient has been proposed with a view to solve such problems (see EP 963751). However, the water repellency, oil repellency, skin-oil resistance, and adhesion to the hair and skin of such a vinyl polymer are still not completely satisfactory.

The inventors arrived at the present invention as a result of in-depth investigations aimed at overcoming the above-described problems. Namely, it is an object of the present invention to provide a cosmetic raw material exhibiting superior compounding stability in cosmetic products and capable of imparting excellent feel on application and surface protective properties to cosmetic products, a cosmetic product exhibiting superior adhesion to the hair and skin obtained by compounding with said cosmetic raw material, and a method for manufacturing the cosmetic product.

The present invention relates to a cosmetic raw material using a vinyl polymer containing carbosiloxane dendritic structures and fluorinated organic groups as its main or most important ingredient, a cosmetic product obtained by compounding with the cosmetic raw material, preferably by combining it with other raw materials or other cosmetic ingredients and a method for manufacturing the cosmetic product, in which the cosmetic raw material is mixed with other cosmetic ingredients or other raw materials.

First of all, explanations are provided regarding the cosmetic raw material of the present invention. The vinyl polymer used in the cosmetic raw material of the present invention is characterized by containing carbosiloxane dendritic structures and fluorinated organic groups. Structures, in which vinylic polymerized units constitute the backbone and carbosiloxane dendritic structures along with fluorinated organic groups are attached in side chains, are particularly preferable. In this invention, the carbosiloxane dendritic structures are high molecular structures obtained by regular high-degree branching from a single silicon atom. Structures represented by the formula(I):

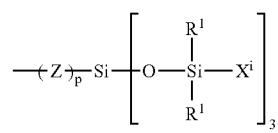

are suggested as a specific example (see EP1055674). In the formula(I), Z is a divalent organic group exemplified by alkylene, arylene, aralkylene, ester-containing divalent organic groups, ether-containing divalent organic groups, ketone-containing divalent organic groups, and amide-containing divalent organic groups. Among the above, organic groups represented by the following formulas are preferable.

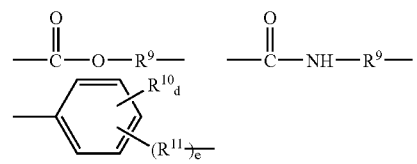

where $R^9$ is an alkylene group with 1 to 10 carbon atoms exemplified by methylene, ethylene, propylene, and butylene. Among the above, methylene and propylene are preferable. $R^{10}$ is an alkyl group with 1 to 10 carbon atoms exemplified by methyl, ethyl, propyl, and butyl. Among the above, methyl is preferable. $R^{11}$ is an alkylene group with 1 to 10 carbon atoms exemplified by methylene, ethylene, propylene, and butylene. Among the above, ethylene is preferable. The subscript <<d>> is an integer of 0 to 4, and <<e>> is 0 or 1. In the formula(I), the subscript <<p>> is 0 or 1. $R^1$ is an aryl or alkyl group with 1 to 10 carbon atoms, with alkyl groups exemplified by methyl, ethyl, propyl, butyl, pentyl, isopropyl, isobutyl, cyclopentyl, and cyclohexyl groups, and aryl groups exemplified by phenyl and naphthyl groups. Among the above, methyl and phenyl are preferable, and methyl is particularly preferable. $X^i$ is a silylalkyl group represented by the following formula(II):

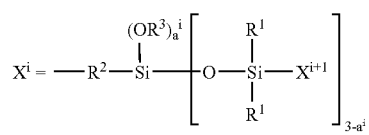

In the formula(II), $R^1$ is the same as above. $R^2$ is an alkylene group with 2 to 10 carbon atoms exemplified by ethylene, propylene, butylene, hexylene, and other linear alkylene groups; methylmethylene, methylethylene, 1-methylpentylene, 1,4-dimethylbutylene, and other branched alkylene groups. Among the above, ethylene, methylethylene, hexylene, 1-methylpentylene, and 1,4-dimethylbutylene are preferable. $R^3$ is an alkyl group with 1 to 10 carbon atoms exemplified by methyl, ethyl, propyl, butyl, and isopropyl. $X^{i+1}$ is a group selected from the group comprising hydrogen atoms, aryl groups and alkyl groups with 1 to 10 carbon atoms, and the above-mentioned silylalkyl groups $X^i$, with the alkyl and aryl groups exemplified by the same groups as the above-described $R^1$. The superscript <<i>> is an integer of 1 to 10 indicating the generation of the silylalkyl group, starting in each carbosiloxane dendritic structure with a value of 1 for the $X^i$ group in the formula(I), and <<$a^i$>> is an integer of 0 to 3.

On the other hand, groups obtained by substituting fluorine atoms for some or all of the hydrogen atoms of methyl, ethyl, propyl, isopropyl, butyl, isobutyl, tert-butyl, pentyl, neopentyl, hexyl, cyclohexyl, heptyl, octyl, nonyl, decyl, undecyl, dodecyl, tridecyl, tetradecyl, hexadecyl, octadecyl, and other alkyl groups with 1 to 20 carbon atoms, as well as alkyloxyalkylene groups with 6 to 22 carbon atoms, are suggested as the fluorinated organic groups.

Groups represented by the formula: $-(CH_2)_x-(CF_2)_y-R^{13}$ are suggested as examples of fluoroalkyl groups obtained by substituting fluorine atoms for the hydrogen atoms of alkyl groups. In the formula, the subscript <<x>> is 0, 1, 2, or 3 and <<y>> is an integer of 1 to 20. $R^{13}$ is an atom or group selected from a hydrogen atom, a fluorine atom, $-CH(CF_3)_2-$ or $-CF(CF_3)_2$. Such fluorine-substituted alkyl groups are exemplified by linear or branched polyfluoroalkyl or perfluoroalkyl groups represented by the formulas shown below.

$-CF_3$, $-C_2F_5$, $-nC_3F_7$, $-CF(CF_3)_2$, $-nC_4F_9$, $-CF_2CF(CF_3)_2$, $-nC_5F_{11}$, $-nC_6F_{13}$, $-nC_8F_{17}$, $-CH_2CF_3$, $-CH(CF_3)_2$, $-CH_2CH(CF_3)_2$, $-CH_2(CF_2)_2F$, $-CH_2(CF_2)_3F$, $-CH_2(CF_2)_4F$, $-CH_2(CF_2)_6F$, $-CH_2(CF_2)_8F$, $-CH_2CH_2CF_3$, $-CH_2CH_2(CF_2)_2F$, $-CH_2CH_2(CF_2)_3F$, $-CH_2CH_2(CF_2)_4F$, $-CH_2CH_2(CF_2)_6F$, $-CH_2CH_2(CF_2)_8F$, $-CH_2CH_2(CF_2)_{10}F$, $-CH_2CH_2(CF_2)_{12}F$, $-CH_2CH_2(CF_2)_{14}F$, $-CH_2CH_2(CF_2)_{16}F$, $-CH_2CH_2CH_2CF_3$, $-CH_2CH_2CH_2(CF_2)_2F$, $-CH_2CH_2CH_2(CF_2)_2H$, $-CH_2(CF_2)_4H$, and $-CH_2CH_2(CF_2)_3H$.

Groups represented by the general formula $-CH_2CH_2-(CF_2)_m-CFR^{14}-[OCF_2CF(CF_3)]_n-OC_3F_7$ are suggested as fluoroalkyloxyfluoroalkylene groups obtained by substituting fluorine atoms for the hydrogen atoms of alkyloxyalkylene groups. In the formula, the subscript <<m>> is 0 or 1, <<n>> is 0, 1, 2, 3, 4, or 5, and $R^{14}$ is a fluorine atom or $CF_3$. Such fluoroalkyloxyfluoroalkylene groups are exemplified by perfluoroalkyloxyfluoroalkylene groups represented by the formulas shown below. $-CH_2CH_2CF(CF_3)-[OCF_2CF(CF_3)]_n-OC_3F_7$, $-CH_2CH_2CF_2CF_2-[OCF_2CF(CF_3)]_n-OC_3F_7$.

Fluoroalkyl groups in general, and fluoroalkyl groups with 1 to 14 carbon atoms in particular, are preferable among such fluorinated organic groups from the standpoint of improving the oil repellency and skin-oil resistance of the cosmetic raw material of the present invention. In addition, fluoroalkyl groups with 1 to 5 carbon atoms, and, more specifically, groups such as $-CH_2CF_3$, are preferable when it is desirable to reduce stickiness.

To make compounding easier, the number average molecular weight of the vinyl polymer used in the present invention should preferably be between 3,000 and 2,000,000, and, even more preferably, between 5,000 and 800,000. In addition, the polymer can be used in various forms, for example, in liquid, rubber, paste, solid, or powder form. When compounding in a cosmetic product, it is preferable to use it in powder form or in the form of a suspension or solution prepared by dissolving in a solvent.

This type of vinyl polymer is obtained by adding, if desired or necessary, (B) a vinyl monomer that does not have fluorinated organic groups in the molecule to (A) a vinyl monomer containing fluorinated organic groups in the molecule and (C) a carbosiloxane dendrimer containing radical polymerizable organic groups represented by the general formula(III):

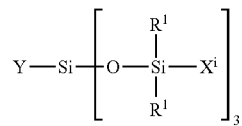

wherein Y is a radical polymerizable organic group and $R^1$ and $X^i$ are the same as above and subjecting them to co-polymerization.

The vinyl monomers (A) containing fluorinated organic groups in the molecule are preferably monomers represented by the general formula: $CH_2=CR^{15}COOR^f$. In the formula, $R^{15}$ is a hydrogen atom or methyl group, $R^f$ is a fluorinated organic group exemplified by the above-described fluoroalkyl and fluoroalkyloxyfluoroalkylene groups. Compounds represented by the formulas shown below are suggested as specific examples of Component (A). In the formulas shown below, <<z>> is an integer of 1 to 4.

$CH_2=CCH_3COO-CF_3$. $CH_2=CCH_3COO-C_2F_5$. $CH_2=CCH_3COO-nC_3F_7$ $CH_2=CCH_3COO-CF(CF_3)_2$. $CH_2=CCH_3COO-nC_4F_9$ $CH_2=CCH_3COO-CF_2\ CF(CF_3)_2$. $CH_2=CCH_3COO-nC_5F_{11}$.

$CH_2=CCH_3COO-nC_6F_{13}$. $CH_2=CCH_3COO-nC_8FI_7$ $CH_2=CCH_3COO-CH_2CF_3$.

$CH_2=CCH_3COO-CH(CF_3)_2$. $CH_2=CCH_3COO-CH_2CH(CF_3)_2$.

$CH_2=CCH_3COO-CH_2\ (CF_2)_2F$.

$CH_2=CCH_3COO-CH_2(CF_2)_3F$. $CH_2=CCH_3COO-CH_2 (CF_2)_4F$.

$CH_2=CCH_3COO-CH_2(CF_2)_6F$. $CH_2=CCH_3COO-CH_2 (CF_2)_8F$.

$CH_2=CCH_3COO-CH_2CH_2CF_3$. $CH_2=CCH_3COO-CH_2CH_2\ (CF_2)_2F$.

$CH_2=CCH_3COO-CH_2CH_2 (CF_2)_3F$. $CH_2=CCH_3COO-CH_2CH_2 (CF_2)_4F$.

$CH_2=CCH_3COO-CH_2CH_2 (CF_2)_6F$. $CH_2=CCH_3COO-CH_2CH_2 (CF_2)_8F$.

$CH_2=CCH_3COO-CH_2CH_2(CF_2)_{10}F$.

$CH_2=CCH_3COO-CH_2CH_2\ (CF_2)_{12}F$.

$CH_2=CCH_3COO-CH_2CH_2(CF_2)_{14}F$.
$CH_2=CCH_3COO-CH_2CH_2(CF_2)_{16}F$.
$CH_2=CCH_3COO-CH_2CH_2CH_2CF_3$.
$CH_2=CCH_3COO-CH_2CH_2CH_2(CF_2)_2F$.
$CH_2=CCH_3COO-CH_2CH_2(CF_2)_2H$.
$CH_2=CCH_3COO-CH_2(CF_2)_4H$.
$CH_2=CCH_3COO-CH_2CH_2(CF_2)_3H$.
$CH_2=CCH_3COO-CH_2CH_2CF(CF_3)-[OCF_2 CF(CF_3)]z-OC_3F_7$.
$CH_2=CCH_3COO-CH_2CH_2CF_2CF_2-[OCF_2CF(CF_3)]z-OC_3F_7$.
$CH_2=CHCOO-CF_3$.  $CH_2=CHCOO-C_2F_5$.
$CH_2=CHCOO-nC_3F_7$. $CH_2=CHCOO-CF(CF_3)_2$.
$CH_2=CHCOO-nC_4F_9$.  $CH_2=CHCOO-CF_2CF(CF_3)_2$.
$CH_2=CHCOO-nC_5F_{11}$.
$CH_2=CHCOO-nC_6F_3$   $CH_2=CHCOO-nC_8F_{17}$.
$CH_2=CHCOO-CH_2CF_3$.
$CH_2=CHCOO-CH(CF_3)_2$   $CH_2=CHCOO-CH_2CH(CF_3)_2$. $CH_2=CHCOO-CH_2(CF_2)_2F$.
$CH_2=CHCOO-CH_2(CF_2)_3F$. $CH_2=CHCOO-CH_2(CF_2)_4F$. $CH_2=CHCOO-CH_2(CF_2)_6F$.
$CH_2=CHCOO-CH_2 (CF_2)_8 F$.  $CH_2=CHCOO-CH_2CH_2CF_3$.
$CH_2=CHCOO-CH_2CH_2(CF_2)_2F$.
$CH_2=CHCOO-CH_2CH_2 (CF_2)_3F$. $CH_2=CHCOO-CH_2CH_2 (CF_2)_4F$.
$CH_2=CHCOO-CH_2CH_2 (CF_2)_6F$. $CH_2=CHCOO-CH_2CH_2 (CF_2)_8F$.
$CH_2=CHCOO-CH_2CH_2(CF_2)_{10}F$. $CH_2=CHCOO-CH_2CH_2(CF_2)_{12}F$.
$CH_2=CHCOO-CH_2CH_2 (CF_2)_{14}F$. $CH_2=CHCOO-CH_2CH_2 (CF_2)_{16}F$.
$CH_2=CHCOO-CH_2CH_2CH_2CF_3$. $CH_2=CHCOO-CH_2CH_2 CH_2 (CF_2)_2F$.
$CH_2=CHCOO-CH_2CH_2CH_2 (CF_2)_2H$. $CH_2=CHCOO-CH_2(CF_2)_4H$.
$CH_2=CHCOO-CH_2CH_2(CF_2)_3H$.
$CH_2=CHCOO-CH_2CH_2CF(CF_3)-[OCF_2 CF(CF_3)]z-OC_3 F_7$.
$CH_2=CHCOO-CH_2CH_2CF_2CF_2-[OCF_2 CF(CF_3)]z-OC_3 F_7$.

Among the above, vinyl polymers represented by the formulas shown below are preferable.

$CH_2=CHCOO-CH_2CH_2 (CF_2)_6F$   $CH_2=CHCOO-CH_2CH_2 (CF_2)_8F$.
$CH_2=CCH_3COO-CH_2CH_2 (CF_2)_6F$. $CH_2=CCH_3COO-CH_2CH_2 (CF_2)_8 F$.
$CH_2=CHCOO-CH_2CF_3$. $CH_2=CCH_3COO-CH_2CF_3$

Vinyl polymers represented by the formulas shown below are particularly preferable.

$CH_2=CHCOO-CH_2CF_3$. $CH_2=CCH_3COO-CH_2CF_3$.

The vinyl monomers (B) that do not contain fluorinated organic groups in the molecule may be any monomers having radical polymerizable vinyl groups, which are exemplified, for instance, by methyl acrylate, methyl methacrylate, ethyl acrylate, ethyl methacrylate, n-propyl acrylate, n-propyl methacrylate, isopropyl acrylate, isopropyl methacrylate, and other lower alkyl acrylates or methacrylates; glycidyl acrylate, glycidyl methacrylate; n-butyl acrylate, n-butyl methacrylate, isobutyl acrylate, isobutyl methacrylate, tert-butyl acrylate, tert-butyl methacrylate, n-hexyl acrylate, n-hexyl methacrylate, n-hexyl acrylate, n-hexyl methacrylate, cyclohexyl acrylate, cyclohexyl methacrylate, 2-ethylhexyl acrylate, 2-ethylhexyl methacrylate, octyl acrylate, octyl methacrylate, lauryl acrylate, lauryl methacrylate, stearyl acrylate, stearyl methacrylate, and other higher acrylates and methacrylates; vinyl acetate, vinyl propionate, and other lower fatty acid vinyl esters; vinyl butyrate, vinyl caproate, vinyl 2-ethylhexanoate, vinyl laurate, vinyl stearate, and other higher fatty acid esters; styrene, vinyltoluene, benzyl acrylate, benzyl methacrylate, phenoxyethyl acrylate, phenoxyethyl methacrylate, vinyl pyrrolidone, and other aromatic vinyl monomers; dimethyl aminoethyl acrylate, dimethyl aminoethyl methacrylate, diethyl aminoethyl acrylate, diethyl aminoethyl methacrylate, and other amino-containing vinyl monomers; acrylamide, methacrylamide, N-methylol acrylamide, N-methylol methacrylamide, N-methoxymethyl acrylamide, N-methoxymethyl methacrylamide, isobutoxymethoxyacrylamide, isobutoxymethoxymethacrylamide, N,N-dimethyl acrylamide, N,N-dimethyl methacrylamide, and other amide-containing vinyl monomers; hydroxyethyl acrylate, hydroxyethyl methacrylate, acrylic acid hydroxypropyl alcohol, methacrylic acid hydroxypropyl alcohol, and other hydroxyl-containing vinyl monomers; acrylic acid, methacrylic acid, itaconic acid, crotonic acid, fumaric acid, maleic acid, and other carboxylic acid-containing vinyl monomers; tetrahydrofurfuryl acrylate, tetrahydrofurfuryl methacrylate, butoxyethyl acrylate, butoxyethyl methacrylate, ethoxydiethylene glycol acrylate, ethoxydiethylene glycol methacrylate, polyethylene glycol acrylate, polyethylene glycol methacrylate, polypropylene glycol monoacrylate, polypropylene glycol monomethacrylate, hydroxybutyl vinyl ether, cetyl vinyl ether, 2-ethylhexyl vinyl ether, and other ether bond-containing vinyl monomers; acryloxypropyltrimethoxysilane, methacryloxypropyltrimethoxysilane, polydimethylsiloxanes containing acryl or methacryl groups at the one of the terminal ends, polydimethylsiloxanes containing alkenylaryl groups at the one of the terminal ends, and other unsaturated group-containing silicone compounds; butadiene; vinyl chloride; vinylidene chloride; acrylonitrile, methacrylonitrile; dibutyl fumarate; maleic anhydride; dodecyl succinic anhydride; acryl glycidyl ether, methacryl glycidyl ether, 3,4-epoxycyclohexylmethyl acrylate, 3,4-epoxycyclohexylmethyl methacrylate; alkali metal salts, ammonium salts, and organic amine salts of acrylic acid, methacrylic acid, itaconic acid, crotonic acid, fumaric acid, maleic acid, and other radical polymerizable unsaturated carboxylic acids, radical polymerizable unsaturated monomers containing sulfonic acid groups such as styrenesulfonic acid as well as their alkali metal salts, ammonium salts, and organic amine salts; quaternary ammonium salts derived from acrylic acid or methacrylic acid such as 2-hydroxy-3-methacryloxypropyl trimethylammonium chloride, methacrylic acid esters of a tertiary amine-containing alcohol such as methacrylic acid diethylamine ester and their quaternary ammonium salts.

In addition, it is also possible to use as vinyl monomers (B) polyfunctional vinyl monomers, which are exemplified, for instance, by trimethylolpropane triacrylate, trimethylolpropane trimethacrylate, pentaerythritol triacrylate, pentaerythritol trimethacrylate, ethylene glycol diacrylate, ethylene glycol dimethacrylate, tetraethylene glycol diacrylate, tetraethylene glycol dimethacrylate, polyethylene glycol diacrylate, polyethylene glycol dimethacrylate, 1,4-butanediol diacrylate, 1,4-butanediol dimethacrylate, 1,6-hexanediol diacrylate, 1,6-hexanediol dimethacrylate, neopentyl glycol diacrylate, neopentyl glycol dimethacrylate, trimethylolpropane trioxyethyl acrylate, trimethylolpropane trioxyethyl methacrylate, tris(2-hydroxyethyl)isocyanurate diacrylate, tris(2-hydroxyethyl)isocyanurate dimethacrylate, tris(2-hydroxyethyl)isocyanurate triacrylate, tris(2-hydroxyethyl)isocyanurate trimethacrylate, polydimethylsiloxane having both ends of the molecular chain blocked by alkenylaryl groups, and other unsaturated group-containing silicone compounds.

As concerns the above-mentioned ratio, in which component (A) and component (B) are co-polymerized, the weight ratio of component (A) to component (B) should be within the range of from 0.1:99.9 to 100:0, and, preferably, within the range of from 1:99 to 100:0.

The carbosiloxane dendrimer (C) is represented by the general formula(III), indicated above. In that formula(III), Y is a radical polymerizable organic group, the type of which is not subject to any special limitations so long as this is an organic group capable of undergoing a radical addition reaction. Acryl and methacryl-containing organic groups, alkenylaryl-containing organic groups, or alkenyl groups with 2 to 10 carbon atoms represented by the general formulas shown below are suggested as specific examples.

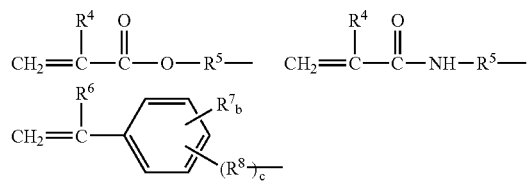

In the formulas, $R^4$ and $R^6$ are hydrogen atoms or methyl groups, $R^5$ and $R^8$ are alkylene groups with 1 to 10 carbon atoms, and $R^7$ is an alkyl group with 1 to 10 carbon atoms. The subscript <<b>> is an integer of 0 to 4, and <<c>> is 0 or 1.

Acryloxymethyl, 3-acryloxypropyl, methacryloxymethyl, 3-methacryloxypropyl, 4-vinylphenyl, 3-vinylphenyl, 4-(2-propenyl)phenyl, 3-(2-propenyl)phenyl, 2-(4-vinylphenyl) ethyl, 2-(3-vinylphenyl)ethyl, vinyl, allyl, methallyl, and 5-hexenyl are suggested as examples of such radical polymerizable organic groups. The superscript <<i>> in the formula (II), which is an integer of 1 to 10, is the generation number of said silylalkyl group, in other words, the number of times the silylalkyl group is repeated. Thus, the carbosiloxane dendrimer of this component with a generation number of 1 is represented by the general formula:

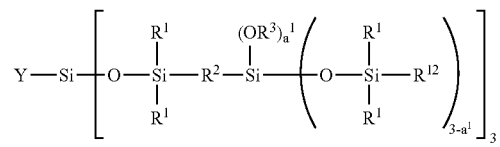

(wherein Y, $R^1$, $R^2$, and $R^3$ are the same as above, and $R^{12}$ is a hydrogen atom or the same as $R^1$ described above. The subscript <<$a^1$>> is an integer of 0 to 3, the average total of <<$a^1$>> per molecule being 0 to 7). Carbosiloxane dendrimers of this component with a generation number of 2 are represented by the general formula:

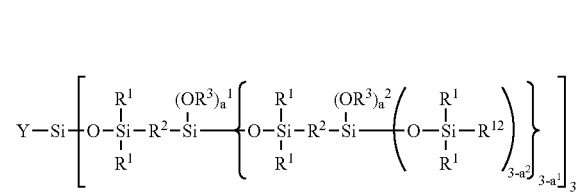

(wherein Y, $R^1$, $R^2$, $R^3$, and $R^{12}$ are the same as above, and the subscripts <<$a^1$>> and <<$a^2$>> are integers of 0 to 3, the average total of <<$a^1$>> and <<$a^2$>> per molecule being 0 to 25).

Carbosiloxane dendrimers of this component with a generation number of 3 are represented by the general formula:

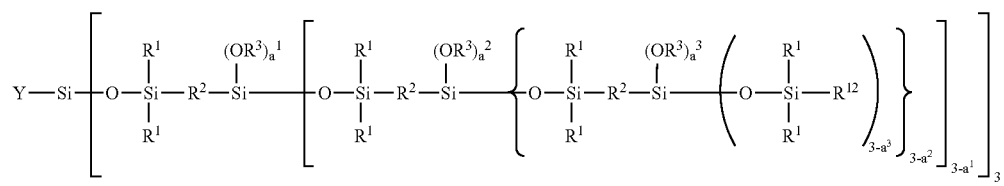

(wherein Y, $R^1$, $R^2$, $R^3$, and $R^{12}$ are the same as above and the subscripts <<$a^1$>>, <<$a^2$>> and <<$a^3$>> are integers of 0 to 3, the average total of <<$a^1$>>, <<$a^2$>), and <<$a^3$>> per molecule being 0 to 79).
Component (C) is exemplified by carbosiloxane dendrimers represented by the average composition formulas shown below.
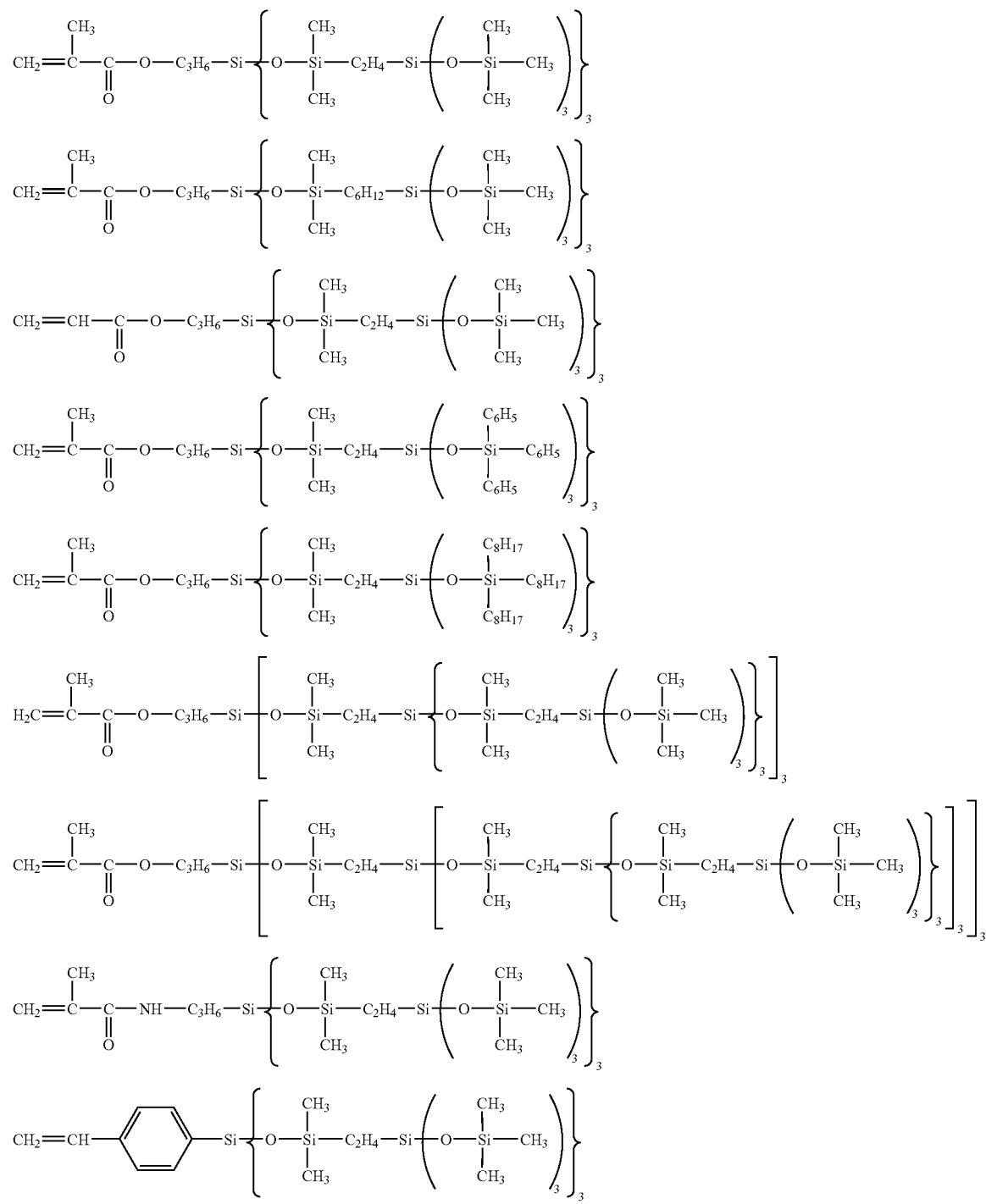

-continued

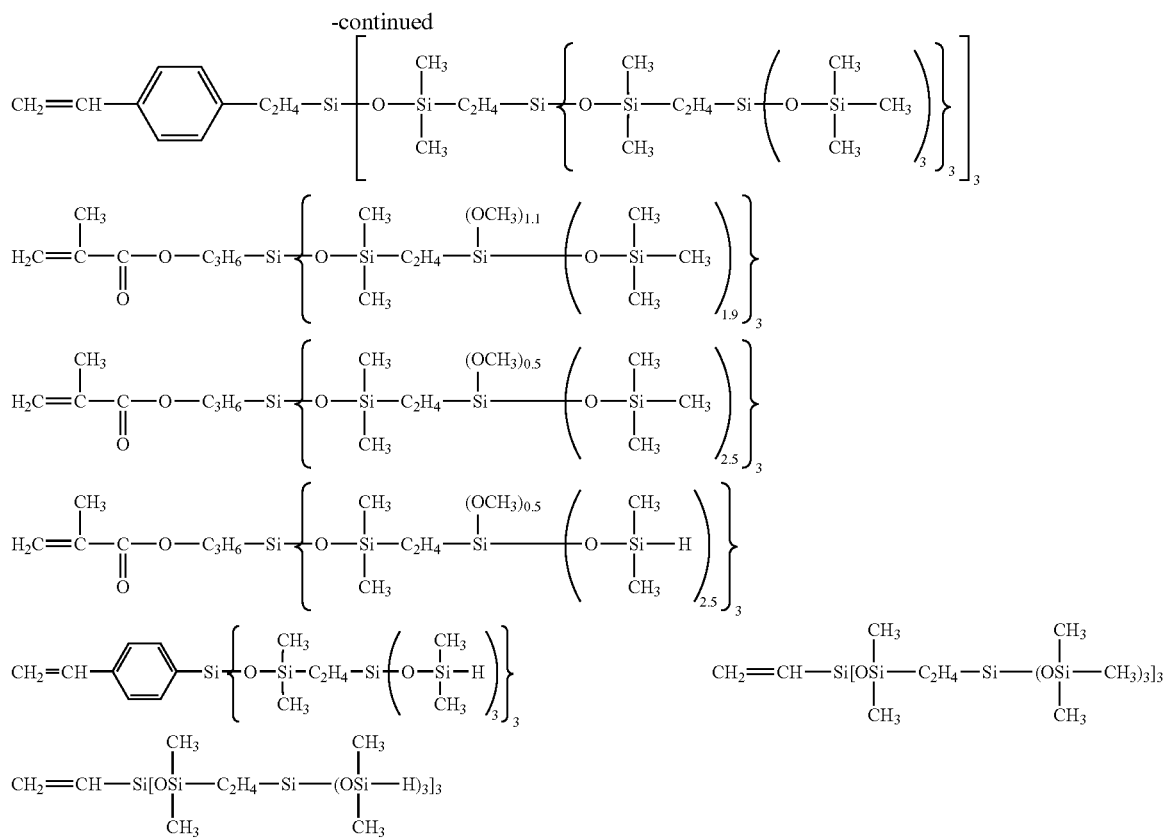

The carbosiloxane dendrimers of component (C) can be prepared using the preparation method for branched siloxane/silalkylene copolymers described in EP1055674. For example, they can be prepared by subjecting alkenyl-containing organic silicon compounds and silicon compounds containing silicon-bonded hydrogen atoms represented by the general formula:

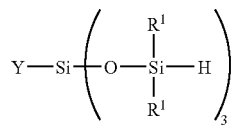

(where $R^1$ and Y are the same as above) to a hydrosilation reaction. For instance, 3-methacryloxypropyl tris(dimethylsiloxy)silane, 3-acryloxypropyl tris(dimethylsiloxy)silane, and 4-vinylphenyl tris(dimethylsiloxy)silane are used as the silicon compounds represented by the formula above. Vinyltris(trimethylsiloxy)silane, vinyltris(dimethylphenylsiloxy)silane, and 5-hexenyltris(trimethylsiloxy)silane are used as the alkenyl-containing organic silicon compounds. In addition, it is preferable to conduct the hydrosilation reaction in the presence of a transition metal catalyst, such as chloroplatinic acid and platinum/vinylsiloxane complex.

The co-polymerization ratio of component (C), in terms of its weight ratio with respect to the total of component (A) and component (B), should be in the range of from 0.1:99.9 to 99.9:0.1, preferably, in the range of from 1:99 to 99:1, and, even more preferably, in the range of from 5:95 to 95:5.

The vinyl polymers used in the present invention are prepared by co-polymerizing the above-described component (A), component (B), and component (C) or by polymerizing component (A) and component (C). Radical polymerization and ion polymerization can be used as the polymerization methods, with radical polymerization being preferable and solution polymerization being especially suitable. Solution polymerization is carried out by reacting the above-described components in a solvent in the presence of a radical initiator for 3 to 20 hours at a temperature of 50 to 150° C. Solvents used at such time are exemplified by hexane, octane, decane, cyclohexane, and other aliphatic hydrocarbons; benzene, toluene, xylene, and other aromatic hydrocarbons; diethyl ether, dibutyl ether, tetrahydrofuran, dioxane, and other ethers; acetone, methyl ethyl ketone, methyl isobutyl ketone, diisobutyl ketone, and other ketones; methyl acetate, ethyl acetate, butyl acetate, isobutyl acetate, and other esters; methanol, ethanol, isopropyl alcohol, butanol, and other alcohols; octamethylcyclotetrasiloxane, decamethylcyclopentasiloxane, hexamethyldisiloxane, octamethyltrisiloxane, and other organosiloxane oligomers. The radical initiators are publicly known conventional compounds used for radical polymerization, specifically exemplified by 2,2'-azobis(isobutyronitrile), 2,2'-azobis(2-methylbutyronitrile), 2,2'-azobis(2,4-dimethylvaleronitrile), and other azobis compounds; benzoyl peroxide, lauroyl peroxide, tert-butyl peroxybenzoate, tert-butyl peroxy-2-ethylhexanoate, and other organic peroxides. The radical initiators can be used singly or in combination as two or more initiators mixed together. The amount of the radical initiator is preferably in the range of from 0.1 to 5 parts by weight per 100 parts by weight of the total of the above-described component (A) to component (C). In addition, chain transfer agents can be added during polymerization. Specific example of the chain transfer agents include 2-mercaptoethanol, butylmercaptan, n-dodecylmercaptan, 3-mercaptopropyltrimethoxysilane, mercaptopropyl-containing polydimethylsiloxanes, and other mercapto compounds; methylene chloride, chloroform, carbon tetrachloride, butyl bromide, 3-chloropropyltrimethoxysilane, and other halogen compounds. In addition, after polymerization, it is preferable to remove residual unreacted vinyl monomers by treating the polymer under reduced pressure and heating.

In addition, in order to further improve the adherence or adhesion of the vinyl polymer to the skin and hair, as well as impart it with suitable properties for easy washability after application, amino groups can be introduced in the side chains of the vinyl polymer by using, as part of component (B), vinyl monomers containing amino groups, such as dimethyl aminoethyl acrylate, dimethyl aminoethyl methacrylate, diethyl aminoethyl acrylate, and diethyl aminoethyl methacrylate, and then performing modification with potassium monochloroacetate, ammonium monochloroacetate, aminomethylpropanol salt of monochloroacetic acid, triethanolamine salt of monobromoacetic acid, sodium monochloropropionate, and other alkali metal salts of halogenated fatty acids; otherwise, carboxylic acid groups can be introduced in the side chains of the vinyl polymer by using, as part of component (B), vinyl monomers containing carboxylic acids, such as acrylic acid, methacrylic acid, itaconic acid, crotonic acid, fumaric acid, and maleic acid, etc., and then neutralizing the product with triethylamine, diethylamine, triethanolamine, and other amines.

The cosmetic raw material of the present invention uses the above-described vinyl polymer containing carbosiloxane dendritic structures and fluorinated organic groups as its main or most important ingredient. Solutions or dispersions obtained by adding liquids selected from the group comprising silicone oil, organic oil, alcohol, and water to the vinyl polymer are suggested as examples of such materials. The viscosity of such a solution or dispersion at 25° C. is preferably in the range of from 10 to 1,000,000,000 mPa·s, and, even more preferably, in particular, from the standpoint of improving the feel of the cosmetic product, in the range of from 100 to 500,000,000 mPa·s. In addition, the concentration of the vinyl polymer in the dispersion or solution is typically in the range of from 0.1 wt % to 95 wt %, and, preferably, in the range of from 1 wt % to 85 wt %. Furthermore, to make compounding and handling easier, it should preferably be in the range of from 5 wt % to 75 wt %.

Examples of the silicone oils include, for instance, dimethylpolysiloxane having both ends of the molecular chain blocked by trimethylsiloxy groups, dimethylsiloxane/methylphenylsiloxane copolymer having both ends of the molecular chain blocked by trimethylsiloxy groups, dimethylsiloxane/methyl(3,3,3-trifluoropropyl)siloxane copolymer having both ends of the molecular chain blocked by trimethylsiloxy groups, and other linear non-reactive silicone oils, as well as cyclic compounds such as hexamethylcyclotrisiloxane, octamethylcyclotetrasiloxane, decamethylcyclopentasiloxane, and dodecamethylcyclohexasiloxane. In addition to the above-mentioned non-reactive silicone oils, one may use modified polysiloxanes having polyether, amino, silanol, and other functional groups in the side chains or at the terminal ends of the molecular chain.

Examples of the organic oils include, for instance, liquid paraffin, isoparaffin, hexyl laurate, isopropyl myristate, myristyl myristate, cetyl myristate, 2-octyldodecyl myristate, isopropyl palmitate, 2-ethylhexyl palmitate, butyl stearate, decyl oleate, 2-octyldodecyl oleate, myristyl lactate, cetyl lactate, lanolin acetate, stearyl alcohol, oleyl alcohol, avocado oil, almond oil, olive oil, cacao butter, jojoba oil, sesame oil, soybean oil, Camellia oil, squalane, persic oil, castor oil, mink oil, cottonseed oil, coconut oil, egg yolk oil, beef tallow, pork fat, polypropylene glycol monooleate, neopentyl glycol-2-ethylhexanoate, and other glycol ether oils; isostearic acid triglyceride, coconut oil fatty acid triglyceride, and other polyhydric alcohol ester oils; polyoxyethylene lauryl ether, polyoxypropylene cetyl ether, and other polyoxyalkylene ether oils.

Although any alcohols used in cosmetic raw materials may be utilized, methanol, ethanol, butanol, isopropyl alcohol, and other lower alcohols are preferable.

The vinyl polymer solution or suspension used in the cosmetic raw material of the present invention can be easily prepared by mixing silicone oil, organic oil, alcohol, or water with the vinyl polymer. In addition, these liquids may be present during the polymerization of the vinyl polymer. In this case, it may be necessary to completely eliminate their odor by removing all residual unreacted vinyl monomers by subjecting the solution or dispersion to heat treatment under normal or reduced pressure. Moreover, pigments such as iron oxide and particles of inorganic oxides, such as titanium oxide, silicon oxide, mica, talc, etc., which are allowed to be used as cosmetic ingredients in cosmetic materials, can be compounded or combined with the solutions and dispersions. In addition, in case of dispersions, surfactants may be added in order to improve the dispersibility of the vinyl polymer. Such surfactants are exemplified by hexylbenzenesulfonic acid, octylbenzenesulfonic acid, decylbenzenesulfonic acid, dodecylbenzensulfonic acid, cetylbenzenesulfonic acid, myristylbenzenesulfonic acid, and their sodium salts and other anionic surfactants; octyltrimethylammonium hydroxide, dodecyltrimethylammonium hydroxide, hexadecyltrimethylammonium hydroxide, octyldimethylbenzylammonium hydroxide, decyldimethylbenzylammonium hydroxide, dioctadecyldimethylammonium hydroxide, tallow trimethylammonium hydroxide, coconut oil trimethylammonium hydroxide, and other cationic surfactants; nonionic surfactants based on polyoxyalkylene alkyl ethers, polyoxyalkylene alkyl phenols, polyoxyalkylene alkyl esters, polyoxyalkylene sorbitan esters, polyesters and ethylene oxide adducts of polyethylene glycol, polypropylene glycol, and diethylene glycol trimethylnonanol; as well as mixtures of two or more of the above surfactants. In such dispersions, the average particle size of the vinyl polymer is preferably in the range of from 0.001 to 100 μm, and, even more preferably, in the range of from 0.01 to 50 μm. This is due to the fact that if the average particle size falls outside the indicated ranges, the feel produced on application by cosmetic products compounded with the polymer, and, in particular, finger and skin feel, as well as its spreadability, tend to be insufficient.

The cosmetic raw material of the present invention as described above is characterized by exhibiting superior stability in cosmetic products, imparting excellent feel on application and surface protective properties to cosmetic products, and, furthermore, improving their water repellency and oil repellency. In particular, when used in skin cosmetics, it has the advantage of superior water repellency, gas and moisture permeability, as well as the advantage of being unlikely to cause an unnatural, sticky skinfeel while imparting a clean and neat sensation, and, when used as a hair cosmetic material, has the advantage of imparting water repellency and hair-setting properties. In addition, because of its superior skin-oil resistance, it is characterized by significantly improving adhesion to the skin and hair. Thus, the cosmetic raw material of the present invention is suitable for use as a raw material for skin cosmetics and hair cosmetics.

Next, explanations are provided regarding the cosmetic product of the present invention. In a preferred aspect of the invention, the cosmetic product of the present invention is prepared by adding the above-mentioned cosmetic raw material and consists of the cosmetic raw material of the present invention and other cosmetic ingredients or raw materials. There are no limitations concerning the type etc. of the cosmetic product of the present invention so long as it is normally called a cosmetic product or cosmetic material. Specifically, skin cosmetic materials, for instance, are exemplified by soaps, body shampoos, facial cleansing creams, and other cleansing cosmetic products; skin lotion, creams, cosmetic milk, packs, and other basic cosmetic products; face powders, foundations, and other base makeup cosmetic products, lipstick, cheek rouge, eye shadow, eyeliner, mascara, and other cosmetic products for the care of the eyes and eyebrows; nail polish, and other nail cosmetic products; depilating agents, shaving lotions, anti-perspirants and deodorants, sunburn preventives, and other special cosmetic products; perfumes, eau de cologne, and other scented cosmetic products. In addition, shampoos, hair rinses, hair treatments, permanent wave agents, hair dressing agents, hair-growing agents, hair tonics, hair dyes, etc. are suggested as hair cosmetic materials. Furthermore, toothpastes and bathing agents are suggested as other cosmetic products. The forms, in which the cosmetic product is used, are exemplified by water base liquid formulations, oil base liquid formulations, milk formulations, crime formulations, foam formulations, semi-solid formulations, solid formulations, and powders. In addition, the product can be atomized in spray form.

Other cosmetic raw materials forming part of the cosmetic product of the present invention are exemplified, for instance, by avocado oil, almond oil, olive oil, cacao butter, beef tallow, sesame oil, wheat germ oil, safflower oil, shea butter, turtle oil, camellia oil, persic oil, castor oil, rapeseed oil, macadamia nut oil, mink oil, egg yolk oil, Japanese wax, coconut oil, hydrogenated oil, and other oils and fats; orange roughy oil, carnauba wax, candelilla wax, whale wax, jojoba oil, montan wax, beeswax, lanolin, and other waxes; liquid paraffin, Vaseline, paraffin, ceresin, microcrystalline wax, squalane, and other hydrocarbons; lauric acid, myristic acid, palmitic acid, stearic acid, oleic acid, behenic acid, undecylenic acid, oxystearic acid, linoleic acid, lanolinic acid, synthetic fatty acids, and other higher fatty acids; ethyl alcohol, isopropyl alcohol, lauryl alcohol, cetyl alcohol, cetostearyl alcohol, stearyl alcohol, oleyl alcohol, behenyl alcohol, lanolin alcohol, hydrogenated lanolin alcohol, hexyl decanol, octyl dodecanol, isostearyl alcohol, and other alcohols; cholesterol, dihydrocholesterol, phytosterols, and other sterols; ethyl linoleate, isopropyl myristate, lanolin fatty acid isopropyl ester, hexyl laurate, myristyl myristate, cetyl myristate, octyl dodecyl myristate, decyl oleate, octyl dodecyl oleate, hexyl decyl dimethyloctanoate, glyceryl tri(caprylate/carprate), propylene glycol dioleate, glyceryl triisostearate, glyceryl triisooctanoate, cetyl lactate, myristyl lactate, diisostearyl maleate, and other fatty acid esters; glycerin, propylene glycol, 1,3-butylene glycol, polyethylene glycol, sodium d, 1-pyrrolidonecarboxylate, sodium lactate, sorbitol, sodium hyaluronate, and other humectants; higher fatty acid soaps, sulfuric acid ester salts derived from higher alcohols, N-acyl glutamic acid salts, phosphoric acid ester salts, and other anionic surfactants; cationic surfactants; betaine, amino acid, imidazoline, lecithin-based, and other amphoteric surfactants; polyhydric alcohol ester-based, ethylene oxide condensation-type, and other nonionic surfactants, and other surfactants; iron oxides and other colored pigments; zinc oxides, titanium oxides, zirconium oxides, and other white pigments; mica, talc, cericite, and other skin-colored pigments; dimethylpolysiloxane, methylphenylpolysiloxane, octamethyltetracyclosiloxane, decamethylcyclopentasiloxane, polyether-modified silicone oils, amino-modified silicone oils, trimethylsilicic acid, and other silicone-based materials; purified water; carrageenan, alginic acid, alginic acid salts, gum arabic, traganth gum, pectin, agar-agar, casein, starch, xanthan gum, polyvinyl alcohol, polyvinyl pyrrolidine, poly(meth)acrylic acid and its salts, poly(meth)acrylic acid esters and their derivatives, polyethylene glycol, vinyl acetate resins, and other high molecular compounds; and, furthermore, thickening agents, gelling agents, anti-ageing agents, antistatic agents, pigment-moisturizing agents, dispersing agents, anti-fading agents, anti-precipitation agents, anti-sagging agents, UV absorbers, antibacterial agents, anti-inflammation agents, antiperspirants, antiseptics, perfumes, antioxidants, pH adjusting agents, aerosol agents, and cosmetic treatment components.

In addition, cured silicone particles can be also combined with the cosmetic product of the present invention. Particles of resin-like cured silicone and rubber-like cured silicone are suggested as the above-mentioned cured silicone particles. Resin-like cured silicone particles give a clean feel to the hair and skin while rubber-like cured product particles give an elastic feel to the skin. Resin-like cured silicone particles are prepared by subjecting hydrolyzable silanes or their partial hydrolyzates to hydrolysis and condensation. Rubber-like cured silicone particles are prepared by cross-linking cross-linkable silicone rubber compositions and then grinding the product into powder, or by dispersing cross-linkable silicone rubber compositions in a solvent such as water, etc., cross-linking it, and removing the solvent. Water base suspensions of cured silicone rubber particles are preferable from the standpoint of the ease of compounding. As far as methods of manufacture are concerned, suggested techniques include dispersing rubber-like cured silicone particles in water using surface active agents etc. or dispersing cross-linkable silicone rubber compositions in water and then cross-linking them. In addition, the amount of the added particles should be sufficient to make their content in the cosmetic product fall the range of from 0.1 to 99 wt %, and, more preferably, from 0.2 to 85 wt %.

Because of the particularly good adherence to skin, the cosmetic raw material is also very useful in applications where it may be applied to skin in the form of a topical application, for example a patch, which may be used to deposit or apply a component to the skin. Examples of suitable uses include the use as or in conjunction with a patch to apply cosmetic, or even active ingredients to the skin or via the skin to the body. Such patches are known and have been described in the art together with ways of making and applying them, including for example EP 667382, in which ways of using materials as pressure sensitive adhesives for use as or in conjunction with patches have also been described. The cosmetic raw material could be used for similar purposes, either alone or in conjunction with other suitable ingredients, which have been described in the art. The cosmetic products of the present invention can be prepared by uniformly mixing the above-described cosmetic raw material of the present invention with other cosmetic raw materials. Various mixers and kneaders commonly used in the preparation of cosmetic products can be utilized as mixing means. Such equipment is exemplified, for instance, by Homo-Mixers, paddle mixers, Henschel mixers, Homo-Dispersers, colloid mixers, propeller agitators, Homogenizers, inline type continuous emulsifiers, ultrasonic emulsifiers, and vacuum kneaders.

APPLICATION EXAMPLES

Hereinbelow, the present invention is explained in detail by referring to application examples. In the examples, the word "viscosity" refers to values obtained at 25° C. In addition, the evaluation of the characteristics of the cosmetic raw materials was carried out in accordance with the methods described below.

[Characteristics Of Cosmetic Raw Materials]

Water Repellency

After coating the cosmetic raw material on a glass plate, a vinyl polymer film on its surface was obtained by drying at room temperature to remove the solvent. A drop of water was placed on the surface of the coating film and the contact angle of the water drop was measured. An automatic contact angle meter (from Kyowa Interface Science Co., Ltd.) was used for measurement.

Skin-Oil Resistance 50 ml squalane was placed in a 100-ml beaker, whereupon a vinyl polymer film obtained in the same manner as described above was immersed therein overnight and subsequently subjected to visual assessment of changes in its external appearance. Cases, in which no changes were noted were designated as ○, and cases, in which the coating film was swollen were designated as x.

Glass Transition Temperature

The glass transition temperature was measured using a differential scanning calorimeter (DSC).

Tactile Sensation Produced by Coating Films

After coating the cosmetic raw material on a glass plate, a vinyl polymer film on its surface was obtained by drying at room temperature to remove the solvent. The tactile sensation produced by the surface of the coating film was evaluated by finger touch.

Application Example 1

43 g methyl methacrylate, 17 g n-butyl acrylate, 10 g fluorinated organic group-containing vinyl monomer (1) represented by the formula:

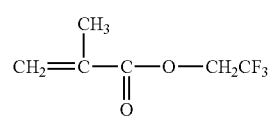

30 g carbosiloxane dendrimer represented by the formula:

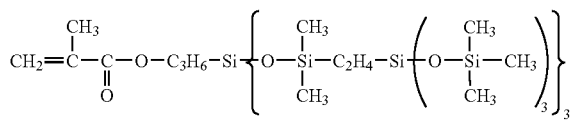

1.5 g 2,2'-azobis-2-methylbutyronitrile (from Otsuka Chemical Co., Ltd.), and 100 g toluene were placed in a 300-ml 4-necked flask fitted with an agitator, a temperature gauge, and a reflux tube and stirred for 6 hours under heating at 70 to 80° C. in a nitrogen atmosphere. After stirring, the product of the reaction was analyzed using gas chromatography, which showed that a vinyl polymer had been obtained at a polymer conversion ratio of 97%. The toluene solution of the vinyl polymer was subjected to 30-min. heat treatment at 140° C. at a reduced pressure of 10 mm Hg to remove the toluene and unreacted monomer. A dispersion of the vinyl polymer containing 20 wt % of nonvolatile matter (hereinafter referred to as "cosmetic raw material (A)") was prepared by adding 80 g cyclic dimethyl silicone (5-mer) to 20 g of the thus obtained vinyl polymer having carbosiloxane dendritic structures and fluorinated organic groups. Its characteristics are listed in Table 1.

Application Example 2

23 g methyl methacrylate, 17 g n-butyl acrylate, 30 g fluorinated organic group-containing vinyl monomer (1) used in Application Example 1, 30 g carbosiloxane dendrimer used in Application Example 1, 1.5 g 2,2'-azobis-2-methylbutyronitrile (from Otsuka Chemical Co., Ltd.), and 100 g toluene were placed in a 300-ml 4-necked flask fitted with an agitator, a temperature gauge, and a reflux tube and stirred for 6 hours under heating at 70 to 80° C. in a nitrogen atmosphere. After stirring, the product of the reaction was analyzed using gas chromatography, which showed that a vinyl polymer had been obtained at a polymer conversion ratio of 96%. The toluene solution of the vinyl polymer was subjected to 30-min. heat treatment at 140° C. at a reduced pressure of 10 mm Hg to remove the toluene and unreacted monomer. A dispersion of the vinyl polymer containing 20 wt % of nonvolatile matter (hereinafter referred to as "cosmetic raw material (B)") was prepared by adding 80 g cyclic dimethyl silicone (5-mer) to 20 g of the thus obtained vinyl polymer having carbosiloxane dendritic structures and fluorinated organic groups. Its characteristics are listed in Table 1.

Application Example 3

43 g methyl methacrylate, 17 g n-butyl acrylate, 10 g fluorinated organic group-containing vinyl monomer (2) represented by the formula:

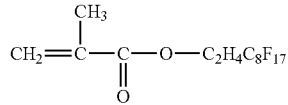

30 g carbosiloxane dendrimer used in Application Example 1, 1.5 g 2,2'-azobis-2-methylbutyronitrile (from Otsuka Chemical Co., Ltd.), and 100 g toluene were placed in a 300-ml 4-necked flask fitted with an agitator, a temperature gauge, and a reflux tube and stirred for 6 hours under heating at 70 to 80° C. in a nitrogen atmosphere. After stirring, the product of the reaction was analyzed using gas chromatography, which showed that a vinyl polymer had been obtained at a polymer conversion ratio of 96%. The toluene solution of the vinyl polymer was subjected to 30-min. heat treatment at 140° C. at a reduced pressure of 10 mm Hg to remove the toluene and unreacted monomer. A dispersion of the vinyl polymer containing 20 wt % of nonvolatile matter (hereinafter referred to as "cosmetic raw material (C)") was prepared by adding 80 g cyclic dimethyl silicone (5-mer) to 20 g of the thus obtained vinyl polymer having carbosiloxane dendritic structures and fluorinated organic groups. Its characteristics are listed in Table 1.

Application Example 4

43 g methyl methacrylate, 17 g n-butyl acrylate, 15 g methacrylic acid, 10 g fluorinated organic group-containing vinyl monomer (1) used in Application Example 1, 15 g carbosiloxane dendrimer used in Application Example 1, 1.5 g 2,2'-azobis-2-methylbutyronitrile (from Otsuka Chemical Co., Ltd.), and 100 g isopropyl alcohol were placed in a 300-ml 4-necked flask fitted with an agitator, a temperature gauge, and a reflux tube and stirred for 6 hours under heating at 70 to 80° C. in a nitrogen atmosphere. After stirring, the product of the reaction was analyzed using gas chromatography, which showed that a vinyl polymer had been obtained at a polymer conversion ratio of 95%. The isopropyl alcohol solution of the vinyl polymer was subjected to 30-min. heat treatment at 140° C. at a reduced pressure of 10 mm Hg to remove the isopropyl alcohol and unreacted monomer. After adding 20 g ethanol to 20 g of the thus obtained vinyl polymer having carbosiloxane dendritic structures and fluorinated organic groups and making a dispersion, 3.68 g triethanolamine was added thereto. Subsequently, a dispersion of the vinyl polymer containing 20 wt % of nonvolatile matter (hereinafter referred to as "cosmetic raw material (D)") was prepared by further adding 74.72 g ethanol. Its characteristics are listed in Table 1.

Comparative Example 1

53 g methyl methacrylate, 17 g n-butyl acrylate, 30 g carbosiloxane dendrimer used in Application Example 1, 1.5 g 2,2'-azobis-2-methylbutyronitrile (from Otsuka Chemical Co., Ltd.), and 100 g toluene were placed in a 300-ml 4-necked flask fitted with an agitator, a temperature gauge, and a reflux tube and stirred for 6 hours under heating at 70 to 80° C. in a nitrogen atmosphere. After stirring, the product of the reaction was analyzed using gas chromatography, which showed that a vinyl polymer had been obtained at a polymer conversion ratio of 97%. The toluene solution of the vinyl polymer was subjected to 30-min. heat treatment at 140° C. at a reduced pressure of 10 mm Hg to remove the toluene and unreacted monomer. A dispersion of the vinyl polymer containing 20 wt % of nonvolatile matter (hereinafter referred to as "cosmetic raw material (E)") was prepared by adding 80 g cyclic dimethyl silicone (5-mer) to 20 g of the thus obtained vinyl polymer having carbosiloxane dendritic structures. Its characteristics are listed in Table 1.

Comparative Example 2

53 g methyl methacrylate, 17 g n-butyl acrylate, 15 g methacrylic acid, 15 g carbosiloxane dendrimer used in Application Example 1, 1.5 g 2,2'-azobis-2-methylbutyronitrile (from Otsuka Chemical Co., Ltd.), and 100 g isopropyl alcohol were placed in a 300-ml 4-necked flask fitted with an agitator, a temperature gauge, and a reflux tube and stirred for 6 hours under heating at 70 to 80° C. in a nitrogen atmosphere. After stirring, the product of the reaction was analyzed using gas chromatography, which showed that a vinyl polymer had been obtained at a polymer conversion ratio of 95%. The isopropyl alcohol solution of the vinyl polymer was subjected to 30-min. heat treatment at 140° C. at a reduced pressure of 10 mm Hg to remove the isopropyl alcohol and unreacted monomer. After adding 20 g ethanol to 20 g of the thus obtained vinyl polymer having carbosiloxane dendritic structures and making a dispersion, 3.68 g triethanolamine was added thereto. Subsequently, a dispersion of the vinyl polymer containing 20 wt % of nonvolatile matter (hereinafter referred to as "cosmetic raw material (F)") was prepared by further adding 74.72 g ethanol. Its characteristics are listed in Table 1.

3.8 parts by weight of castor oil, and 8 parts by weight of glyceryl triisostearate were mixed under heating at 85° C. After that, an oil base liquid lipstick was prepared by further adding 0.1 parts by weight of an anti-oxidant, 0.1 parts by weight of fragrance, 2.0 parts by weight of silicone-treated titanium oxide, 2 parts by weight of Red No. 201, 1 part by weight of Red No. 202, and 3 parts by weight of Yellow No. 4 aluminum lake, uniformly mixing the ingredients, deaerating the mixture, and filling a container with it. The thus obtained lipstick was evaluated in accordance with the methods described below. The results are shown in Table 2.

In addition, no changes in the external appearance of the lipstick were noted after allowing it to stand for 3 months at room temperature, which confirmed the excellent compounding stability of the cosmetic raw material of the present invention.

Feel on Application

A group of 10 panelists applied the lipstick to the lips and evaluated its spreadability, stickiness, and moisturizing feel produced. The results of the evaluation were represented in the following manner: cases, in which 8 to 10 people reported that the lipstick was easily spreadable, non-sticky, and produced a moisturized skinfeel, were designated as ○, those, in which 4 to 7 people reported the same, were designated as Δ, and those, in which 3 or fewer people reported the same, were designated as x.

TABLE 1

|  | Application Examples | | | | Comparative Examples | |
| --- | --- | --- | --- | --- | --- | --- |
|  | 1 | 2 | 3 | 4 | 1 | 2 |
| Cosmetic raw material | A | B | C | D | E | F |
| Methyl methacrylate | 43 parts | 23 parts | 43 parts | 43 parts | 53 parts | 53 parts |
| n-Butyl acrylate | 17 parts | 17 parts | 17 parts | 17 parts | 17 parts | 17 parts |
| Methacrylic acid | — | — | — | 15 parts | — | 15 parts |
| Carbosiloxane dendrimer | 30 parts | 30 parts | 30 parts | 15 parts | 30 parts | 15 parts |
| Fluorinated organic group-containing vinyl monomer (1) | 10 parts | 30 parts | — | 10 parts | — | — |
| Fluorinated organic group-containing vinyl monomer (2) | — | — | 10 parts | — | — | — |
| 2,2'-azobis-2-methylbutyronitrile | 1.5 parts | 1.5 parts | 1.5 parts | 1.5 parts | 1.5 parts | 1.5 parts |
| Polymerization solvent | Toluene, 100 parts | Toluene, 100 parts | Toluene, 100 parts | IPA, 100 parts | Toluene, 100 parts | IPA, 100 parts |
| Water repellency (contact angle) | 109 | 109 | 112 | 109 | 107 | 107 |
| Skin-oil resistance | ○ | ○ | ○ | ○ | X | X |
| Glass transition temperature (° C.) | 47 | 32 | 21 | No meas. | 46 | No meas. |
| Tactile sensation produced by coating film | Excellent | Excellent | Slight stickiness noted | Excellent | Excellent | Excellent |

Application Example 5

<Lipstick>

55 parts by weight of cosmetic raw material (A), 20 parts by weight of a dimethylpolysiloxane with a viscosity of 2 mPa·s having both ends of the molecular chain blocked by trimethylsiloxy groups, 5 parts by weight of liquid lanolin, Color Transfer After applying the lipstick to the lips, a group of 10 panelists pressed a piece of tissue paper to the lips for 5 seconds and evaluated the presence/absence of color transfer. The results of the evaluation were represented in the following manner: cases, in which 8 to 10 people reported that no traces of the lipstick were noticed on the tissue paper, were designated as ◯, those, in which 4 to 7 people reported the same, were designated as Δ, and those, in which 3 or fewer people reported the same, were designated as x.

Long-term Adhesion

A group of 10 panelists applied the lipstick to the lips and performed work indoors for 8 hours at a temperature of 28 to 32° C. and a humidity of 60% or higher, whereupon the presence/absence of remainders of lipstick on the lips was confirmed by finger touch. The results of the evaluation were represented in the following manner: cases, in which 8 to 10 people reported remainders of adhered lipstick, were designated as ◯, those, in which 4 to 7 people reported the same, were designated as Δ, and those, in which 3 or fewer people reported the same, were designated as x.

Application Example 6

<Lipstick>

With the exception of using cosmetic raw material (B) instead of cosmetic raw material (A) in Application Example 5, an oil base liquid lipstick was prepared in the same manner as in Application Example 5. The resultant lipstick was evaluated in the same manner as in Application Example 5, and the results were also listed in Table 2.

In addition, no changes in the external appearance of the lipstick were noted after allowing it to stand for 3 months at room temperature, which confirmed the excellent compounding stability of the cosmetic raw material of the present invention.

Comparative Example 3

<Lipstick>

With the exception of using cosmetic raw material (E) instead of cosmetic raw material (A) in Application Example 5, an oil base liquid lipstick was prepared in the same manner as in Application Example 5. The resultant lipstick was evaluated in the same manner as in Application Example 5, and the results were also listed in Table 2.

TABLE 2

| | Application Example 5 | Application Example 6 | Comparative Example 3 |
|---|---|---|---|
| Spreadability | ◯ | ◯ | ◯ |
| Stickiness | ◯ | ◯ | ◯ |
| Moisturized sensation | ◯ | ◯ | ◯ |
| Color transfer | ◯ | ◯ | ◯ |
| Long-term adhesion | ◯ | ◯ | X |

Application Example 7

<Mascara>

62 parts by weight of cosmetic raw material (B), 15 parts by weight of a dextrin fatty acid ester and 4.5 parts by weight of low-boiling isoparaffin were added to 51 parts of isoparaffin under heating to prepare a dispersion, which was then mixed with 2 parts by weight of hydrophobic treated silicic anhydride, 1.5 parts by weight of organic bentonite, 7 parts by weight of black iron oxide powder, and 10 parts by weight of mica. Mascara was prepared by filling a container with the mixture. The thus obtained mascara was evaluated in accordance with the methods described below. The results were listed in Table 3.

In addition, no changes in the external appearance of the mascara were noted after allowing it to stand for 3 months at room temperature, which confirmed the excellent compounding stability of the cosmetic raw material of the present invention.

Feel on Application

A group of 10 panelists applied the mascara to the eyelashes and evaluated its spreadability. The results of the evaluation were represented in the following manner: cases, in which 8 to 10 people reported that the mascara was easily spreadable, were designated as ◯, those, in which 4 to 7 people reported the same, were designated as Δ, and those, in which 3 or fewer people reported the same, were designated as x.

Curling Properties

A group of 10 panelists applied the mascara to the eyelashes and evaluated its curling properties. The results of the evaluation were represented in the following manner: cases, in which 8 to 10 people reported that the mascara exhibited curling properties, were designated as ◯, those, in which 4 to 7 people reported the same, were designated as Δ, and those, in which 3 or fewer people reported the same, were designated as x.

Long-term Adhesion

A group of 10 panelists applied the mascara to the eyelashes and performed work indoors for 8 hours at a temperature of 28 to 32° C. and a humidity of 60% or higher, whereupon the presence/absence of remainders of mascara was confirmed by finger touch. The results of the evaluation were represented in the following manner: cases, in which 8 to 10 people reported presence of remainders of mascara, were designated as ◯, those, in which 4 to 7 people reported the same, were designated as Δ, and those, in which 3 or fewer people reported the same, were designated as x.

Comparative Example 4

<Mascara>

With the exception of using cosmetic raw material (E) instead of cosmetic raw material (B) in Application Example 7, mascara was prepared in the same manner as in Application Example 7. The resultant mascara was evaluated in the same manner as in Application Example 7, and the results were also listed in Table 3.

TABLE 3

| | Application Example 7 | Comparative Example 4 |
|---|---|---|
| Spreadability | ◯ | ◯ |
| Curling properties | ◯ | ◯ |
| Long-term adhesion | ◯ | X |

Application Example 8

<Nail Polish>

A nail polish was prepared by uniformly mixing 40 parts by weight of cosmetic raw material (A), 15 parts by weight of nitrocellulose, 10 parts by weight of acetyl tributyl citrate, 2 parts by weight of camphor, 5 parts by weight of ethyl acetate, 10 parts by weight of butyl acetate, 16 parts by weight of toluene, 1 part by weight of organic bentonite, and 1 part by weight of pigment, and then filling a container with the mixture. The thus obtained nail polish was evaluated in accordance with the methods described below. The results were listed in Table 4.

In addition, no changes in the external appearance of the nail polish were noted after allowing it to stand for 3 months at room temperature, which confirmed the excellent compounding stability of the cosmetic raw material of the present invention.

Feel on Application

A group of 10 panelists applied the nail polish to the fingernails and evaluated its spreadability and the smoothness of the film formed after drying. The results of the evaluation were represented in the following manner: cases, in which 8 to 10 people reported that the nail polish was easily spreadable and provided excellent smoothness, were designated as ○, those, in which 4 to 7 people reported the same, were designated as Δ, and those, in which 3 or fewer people reported the same, were designated as x.

Long-term Adhesion

A group of 10 panelists applied the nail polish to the fingernails and performed work indoors for 8 hours at a temperature of 28 to 32° C. and a humidity of 60% or higher, whereupon the amount of remaining adhered nail polish was evaluated by visual inspection. The results of the evaluation were represented in the following manner: cases, in which 8 to 10 people reported that the condition of the residual nail polish was the same as immediately upon application, were designated as ○, those, in which 4 to 7 people reported the same, were designated as Δ, and those, in which 3 or fewer people reported the same, were designated as x.

Water Repellency

The nail polish was applied to the fingernails of 10 panelists and dried, whereupon drops of water were placed on the fingernails and water repellency was evaluated based on the extent to which the water drops could stick to or were repelled by the surface. The results of the evaluation were represented in the following manner: cases, in which 8 to 10 people reported that the water drops were repelled by the nail polish, were designated as ○, those, in which 4 to 7 people reported the same, were designated as Δ, and those, in which 3 or fewer people reported the same, were designated as x.

Application Example 9

<Nail Polish>

With the exception of using cosmetic raw material (C) instead of cosmetic raw material (A) in Application Example 8, a nail polish was prepared in the same manner as in Application Example 8. The resultant nail polish was evaluated in the same manner as in Application Example 8, and the results were also listed in Table 4.

Comparative Example 5

<Nail Polish>

With the exception of using cosmetic raw material (E) instead of cosmetic raw material (A) in Application Example 8, a nail polish was prepared in the same manner as in Application Example 8. The resultant nail polish was evaluated in the same manner as in Application Example 8, and the results were also listed in Table 4.

TABLE 4

| | Application Example 8 | Application Example 9 | Comparative Example 5 |
|---|---|---|---|
| Spreadability | ○ | ○ | ○ |
| Coating film smoothness | ○ | ○ | ○ |
| Long-term adhesion | ○ | ○ | X |
| Water repellency | ○ | ○ | Δ |

Application Example 10

<Skin Cream-Type Cosmetic Product>

A skin cream cosmetic material was prepared by putting 15 parts by weight of cosmetic raw material (A), 2 parts by weight of silicone-treated titanium oxide powder, 10 parts by weight of octyl p-methoxycinnamate, 12 parts by weight of a dimethylpolysiloxane with a viscosity of 20 mPa·s having both ends of the molecular chain blocked by trimethylsiloxy groups, 3 parts by weight of polyoxyethylene (40-mol adduct) hydrogenated castor oil, 60 parts by weight of squalane, 5 parts by weight of glycerin, 3 parts by weight of beeswax, a small amount of antiseptic, a small amount of fragrance, and an suitable amount of purified water in a Henschel mixer and stirring the ingredients for 10 minutes at 1500 rpm. The thus obtained cosmetic material was evaluated in accordance with the methods described below. The results were listed in Table 5.

In addition, no changes in the external appearance of the skin cream-type cosmetic material were noted after allowing it to stand for 3 months at room temperature, which confirmed the excellent compounding stability of the cosmetic raw material of the present invention.

Feel on Application

A group of 10 panelists applied the cream to the back of the hands and evaluated its spreadability and skin feel. The results of the evaluation were represented in the following manner: cases, in which 8 to 10 people reported that the cosmetic material was easily spreadable, did not produce an unpleasant sensation and produced an excellent skin feel, were designated as ○, those, in which 4 to 7 people reported the same, were designated as Δ, and those, in which 3 or fewer people reported the same, were designated as x.

Long-term Adhesion

A group of 10 panelists applied the cream to the wrists, spreading and rubbing it in thoroughly with fingers, and performed work indoors for 8 hours at a temperature of 28 to 32° C. and a humidity of 60% or higher. Subsequently, the presence/absence of remainders of adhered cream was evaluated after bending the wrists 50 times. The results of the evaluation were represented in the following manner: cases, in which 8 to 10 people reported that there was some cream left, were designated as ○, those, in which 4 to 7 people reported the same, were designated as Δ, and those, in which 3 or fewer people reported the same, were designated as x.

Water Repellency

After applying and thoroughly spreading the cream on the backs of the hands of 10 panelists, the panelists washed hands with liquid soap and wiped them with a towel. After that, water drops were applied to the backs of the hands and water repellency was evaluated based on the extent to which the water drops could stick to or were repelled by the surface. The results of the evaluation were represented in the following manner: cases, in which 8 to 10 people reported that the water drops were repelled, were designated as ○, those, in which 4 to 7 people reported the same, were designated as Δ, and those, in which 3 or fewer people reported the same, were designated as x.

Comparative Example 6

<Skin Cream-Type Cosmetic Product>

With the exception of using cosmetic raw material (E) instead of 15 parts by weight of cosmetic raw material (A) in Application Example 10, a skin cream-type cosmetic material was prepared in the same manner as in Application Example 10. The cream-type cosmetic material was evaluated in the same manner as in Application Example 10, and the results were also listed in Table 5.

TABLE 5

|  | Application Example 10 | Comparative Example 6 |
| --- | --- | --- |
| Spreadability | ○ | Δ |
| Skin feel | ○ | ○ |
| Long-term adhesion | ○ | X |
| Water repellency | ○ | Δ |

Application Example 11

<Shampoo>

A shampoo was prepared by mixing 20 parts by weight of the disodium salt of sulfosuccinic acid monoester, 2 parts by weight of lauroyl diethanolamide, 5 parts by weight of cosmetic raw material (C), 0.2 parts by weight of fragrance, 0.1 parts by weight of antiseptic, 72.5 parts by weight of purified water, and a trace amount of colorant and filling a container with the mixture. The thus obtained shampoo was evaluated in accordance with the methods described below. The results are shown in Table 6.

Post-Washing Assessment

The gloss and luster of hair was visually evaluated by 10 panelists after washing the hair with the shampoo and drying it. The results of the evaluation were represented in the following manner: cases, in which 8 to 10 people reported that the hair was glossy and lustrous, were designated as ○, those, in which 4 to 7 people reported the same, were designated as Δ, and those, in which 3 or fewer people reported the same, were designated as x.

Long-term Adhesion

The presence/absence of residual shampoo was evaluated by 10 panelists by finger touch after washing the hair with the shampoo and drying it. The results of the evaluation were represented in the following manner: cases, in which 8 to 10 people reported presence of residual adhered shampoo, were designated as ○, those, in which 4 to 7 people reported the same, were designated as Δ, and those, in which 3 or fewer people reported the same, were designated as x.

Water Repellency

After washing the hair with the shampoo and drying it, 10 panelists evaluated water repellency by spraying water drops on the hair and assessing how well the water drops were repelled by the hair. The results of the evaluation were represented in the following manner: cases, in which 8 to 10 people reported good water repellency, were designated as ○, those, in which 4 to 7 people reported the same, were designated as Δ, and those, in which 3 or fewer people reported the same, were designated as x.

Comparative Example 7

<Shampoo>

With the exception of using 5 parts by weight of cosmetic raw material (E) instead of cosmetic raw material (C) in Application Example 11, a shampoo was prepared in the same manner as in Application Example 11. The shampoo was evaluated in the same manner as in Application Example 11, and the results were also listed in Table 6.

TABLE 6

|  | Application Example 11 | Comparative Example 7 |
| --- | --- | --- |
| Gloss and luster after washing hair | ○ | ○ |
| Long-term adhesion | ○ | X |
| Water repellency | ○ | Δ |

Application Example 12

<Hair Spray>

An aerosol hair spray was prepared by mixing 100 parts by weight of cosmetic raw material (D), 50 parts by weight of ethanol, and 35 parts by weight of liquefied petroleum gas under cooling conditions. The thus obtained hair spray was evaluated in accordance with the methods described below. The results are shown in Table 7.

Hair Gloss and Luster 10 panelists had their hair sprayed with the hair spray and styled. After setting, the gloss and luster of the hair were visually evaluated. The results of the evaluation were represented in the following manner: cases, in which 8 to 10 people reported that the hair was glossy and lustrous, were designated as ◯, those, in which 4 to 7 people reported the same, were designated as Δ, and those, in which 3 or fewer people reported the same, were designated as x.

Hair Set Retention Properties

After curling the hair, it was treated with the hair spray. After wearing a wet towel for 5 minutes, 10 panelists evaluated curl retention. The results of the evaluation were represented in the following manner: cases, in which 8 to 10 people reported curl retention, were designated as ◯, those, in which 4 to 7 people reported the same, were designated as Δ, and those, in which 3 or fewer people reported the same, were designated as x.

Long-term Adhesion 10 panelists had their hair sprayed with the hair spray and styled, and, after setting, performed work indoors for 8 hours at a temperature of 28 to 32° C. and a humidity of 60% or higher. Subsequently, the presence/absence of residual hair spray was confirmed by finger touch. The results of the evaluation were represented in the following manner: cases, in which 8 to 10 people reported presence of adhered hair spray, were designated as o, those, in which 4 to 7 people reported the same, were designated as A, and those, in which 3 or fewer people reported the same, were designated as x.

[Comparative Example 8]

<Hair Spray>

With the exception of using cosmetic raw material (F) instead of cosmetic raw material (D) in Application Example 12, a hair spray was prepared in the same manner as in Application Example 12. The hair spray was evaluated in the same manner as in Application Example 12, and the results were also listed in Table 7.

TABLE 7

|  | Application Example 12 | Comparative Example 8 |
| --- | --- | --- |
| Hair gloss and luster | ◯ | ◯ |
| Hair set retention properties | ◯ | X |
| Long-term adhesion | ◯ | X |

What is claimed is:

1. A cosmetic raw material comprising a vinyl polymer, wherein the vinyl polymer is a copolymer selected from the group consisting of A, B and C; and A and C wherein:
   (A) vinyl monomers containing fluorinated organic groups in the molecule,
   (B) vinyl monomers that do not have fluorinated organic groups in the molecule, and
   (C) carbosiloxane dendrimers, having radical polymerizable organic groups, represented by the general formula (III):

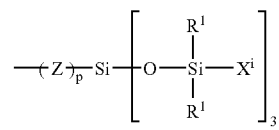

wherein Y is a radical polymerizable organic group, $R^1$ is an aryl or alkyl group with 1 to 10 carbon atoms, and $X^i$ is a silylalkyl group represented by the following formula (II)

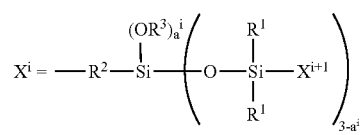

wherein $R^1$ is the same described as above, $R^2$ is an alkylene group with 2 to 10 carbon atoms, $R^3$ is an alkyl group with 1 to 10 carbon atoms, and $X^{i+1}$ is a group selected from the group comprising hydrogen atoms, aryl groups and alkyl groups with 1 to 10 carbon atoms, and silylalkyl groups $X^i$, wherein superscript «i» is an integer of 1 to 10 indicating the generation of the silylalkyl group, starting in each carbosiloxane dendritic structure with a value of 1 for the $X^i$ group in the formula (III), and the subscript «$a^i$» is an integer of 0 to 3, said vinyl polymer having a copolymerization ratio of component (A) to component (B) of 0.1 to 100:99.9 to 0 wt %, and a co-polymerization ratio of the total of component (A) and component (B) to component (C) of 0.1 to 99.9 :99.9 to 0.1 wt %.

2. The cosmetic raw material according to claim 1, wherein the radical polymerizable organic group Y in component (C) is a group selected from the group consisting of organic groups containing acrylic and organic groups containing methacrylic groups represented by the general formula:

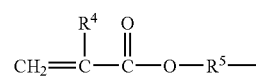

wherein $R^4$ is a hydrogen atom or methyl, and $R^5$ is an alkylene group with 1 to 10 carbon atoms and

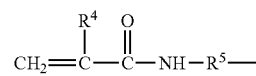

wherein $R^4$ and $R^5$ are as defined above,
organic groups containing alkenylaryl groups represented by the general formula:

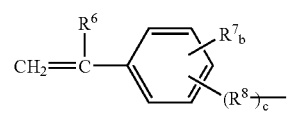

wherein $R^6$ is a hydrogen atom or methyl, $R^7$ is an alkyl group with 1 to 10 carbon atoms, $R^8$ is an alkylene group with 1 to 10 carbon atoms, "b" is an integer of 0 to 4, and "c" is 0 or 1, and, alkenyl groups with 2 to 10 carbon atoms.

3. The cosmetic raw material according to claim 1, which is a solution or dispersion comprising the vinyl polymer containing carbosiloxane dendritic structures and fluorinated organic groups, and a liquid selected from the group consisting of silicone oil, organic oil, alcohol, and water.

4. A cosmetic product obtained by compounding the cosmetic raw material according to claim 1.

5. A cosmetic product according to claim 4, which is intended for topical application to skin.

6. A method for manufacturing a cosmetic product, said method comprising the step of mixing a cosmetic raw material according to claim 1 with other raw materials.

* * * * *

UNITED STATES PATENT AND TRADEMARK OFFICE
CERTIFICATE OF CORRECTION

PATENT NO. : 7,488,492 B2
APPLICATION NO. : 10/496022
DATED : February 10, 2009
INVENTOR(S) : Haruhiko Furukawa et al.

It is certified that error appears in the above-identified patent and that said Letters Patent is hereby corrected as shown below:

In Column 30, line 7, general formula (III), delete "(Z)p" and replace with --(Y)--.

In Column 30, line 31, replace " <<a¹>> " with --<<$a^1$>>-- having the same font size as the rest of the text.

In Column 31, line 4, make "<<C>>" lowercase.

Signed and Sealed this

Twenty-third Day of June, 2009

JOHN DOLL
*Acting Director of the United States Patent and Trademark Office*